United States Patent [19]

Maddry et al.

[11] Patent Number: 5,561,225
[45] Date of Patent: Oct. 1, 1996

[54] POLYNUCLEOTIDE ANALOGS CONTAINING SULFONATE AND SULFONAMIDE INTERNUCLEOSIDE LINKAGES

[75] Inventors: Joseph A. Maddry; Robert C. Reynolds; John A. Secrist; John A. Montgomery, all of Birmingham, Ala.; Peter A. Crooks, Lexington, Ky.

[73] Assignee: Southern Research Institute, Birmingham, Ala.

[21] Appl. No.: 584,570

[22] Filed: Sep. 19, 1990

[51] Int. Cl.$^6$ .............................. C07H 1/00; C07H 19/06; C07H 19/16; C07H 21/00
[52] U.S. Cl. .................. 536/23.1; 536/25.3; 536/27.1; 536/27.13; 536/27.21; 536/27.6; 536/27.81; 536/28.1; 536/28.5; 536/28.53; 536/28.54
[58] Field of Search .................. 536/23, 24, 27, 536/28, 29, 23.1, 25.3, 27.1, 27.13, 27.21, 27.6, 27.81, 28.1, 28.5, 28.53, 28.54

[56] References Cited

U.S. PATENT DOCUMENTS 3,446,793  4/1969  Jones et al. .................. 536/26.13
4,837,311  6/1989  Tam et al. .................. 536/27.14

FOREIGN PATENT DOCUMENTS 8600544  9/1986  WIPO .
8600545  9/1986  WIPO .

OTHER PUBLICATIONS

Schneider et al., Tetrahedron Letters, vol. 31, No. 3, pp. 335–338, Feb. 20, (1990).
CA: vol. 110, No. 17, : 154,780f, 1988.
Musicki et al., "Synthesis of Carbohydrate Sulfonates and Sulfonate Esters", J. Org. Chem., vol. 55, No. 14, pp. 4231–4233 (1990).

*Primary Examiner*—James O. Wilson
*Attorney, Agent, or Firm*—Jacobson, Price, Holman & Stern, PLLC

[57] ABSTRACT

The present invention provides for the preparation and use of ribo- and deoxyribo-nucleosides and polynucleotide analogs. The polynucleotide analogs are made of polynucleosides which contain sulfonate and sulfonamide linkages.

16 Claims, 4 Drawing Sheets

POLYNUCLEOTIDE ANALOGS CONTAINING SULFONATE AND SULFONAMIDE INTERNUCLEOSIDE LINKAGES

The present invention concerns ribo- and deoxyribo-nucleosides and polynucleotide analogs. In particular, this invention is concerned with ribo- and deoxyribo-nucleosides and polynucleotide analogs which contain sulfonate and sulfonamide linkages.

Polynucleotides and polynucleotide analogs have numerous biological, biochemical, and medicinal applications. It is known to use polynucleotides and polynucleotide analogs as antiviral drugs, genetic probes, agents for transcription or translation arrest, and ligands for nucleic acid binding proteins and receptors. See Marcus-Sekura, *Analytical Biochemistry* 172, 289 (1988); Noble et al., *Nucl. Acids Res.* 12, 3387 (1984); Stein et al., *Cancer Res.* 48, 2659 (1988); and Paoletti, *Anti-Cancer Drug Design* 2, 325 (1988).

The Polynucleotide analogs with which this invention is concerned are polynucleosides which contain non-phosphate internucleoside linkages. Known non-phosphate internucleoside linkages include alkyl- and arylphosphonates (Smith et al., *Proc. Natl. Acad. Sci. USA* 83, 2787 (1986)), phosphoramidates (Agrawal et al., *Proc. Natl. Acad. Sci USA* 85, 7079 (1989)), carbamates (Stirchak et al., *J. Org. Chem.* 52 4202 (1987)), dialkylsiloxanes (Cormier et al., *Nucl. Acids Res.* 16, 4583 (1988), phosphorothioates (Gal et al., *J. Biol. Chem.* 264, 11521 (1989), and phosphorodithioates (Grandas et al., *Tetrahedron Lett.* 30, 543 (1989)).

Polynucleotide analogs which contain non-phosphate internuceloside linkages are generally advantageous because of enhanced intracellular stability. The non-ionic linkages thus far disclosed, however, suffer from limitations which include insufficient aqueous solubility, poor interstrand hybridization and duplex formation, and diastereoisomerism which leads to inseparable mixtures of compounds and resultant dilution of biological potency.

According to the present invention there is provided a nucleotide analog wherein the 5' carbon is covalently bonded to a group of the formula —$CH_2SO_2OH$ or =$CHSO_2OH$ and a polynucleotide analog wherein the 3' and 5' ends of adjacent nucleosides therein are linked through moieties as in the formula

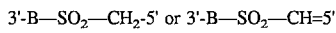

3'-B—$SO_2$—$CH_2$-5' or 3'-B—$SO_2$—CH=5' wherein B is independently in each moiety oxygen, $NHR_3$ with $R_3$ being hydrogen, $C_{1-5}$ alkyl optionally substituted by amino or hydroxy, piperidinyl, piperazinyl, morpholinyl, phenyl, benzyl, allyl, acetyl, or benzoyl.

The polynucleotide analogs of the present invention can be used as antisense agents. That is, the polynucleotide analogs of the present invention are analogs which are complementary to natural nucleic acid base sequences. The analogs can hybridize with the natural sequence which will inhibit or alter the normal function of the natural sequence. (See Weintraub, "Antisense RNA and DNA", *Scientific American*, January 1990, 40–46; and *Oligonucleotides: Antisense Inhibitors of Gene Expression*, Cohen, ed., CRC Press, Boca Raton, Fla. (1989).)

Specifically, the polynucleotide analogs of the present invention can be used as chemotherapeutic agents (see Stein et al., *Cancer Research* 48, 2659–2668 (1988); Rothenberg et al., *Journal of the National Cancer Institute* 81, 1539–1544 (1989)), antiparasitics targeted against other organisms, and as molecular biological, biochemical, and genetic probes. The polynucleotide analogs of the present invention have an advantage over other non-phosphorus linked polynucleotides in that they have the ability to adjust to the natural pitch and curvature of the DNA helix.

The drawings detail synthetic methods which can be used to form the nucleosides and polynucleotide analogs of the present invention.

The nucleotide analog of the present invention is preferably a nucleoside of the formula

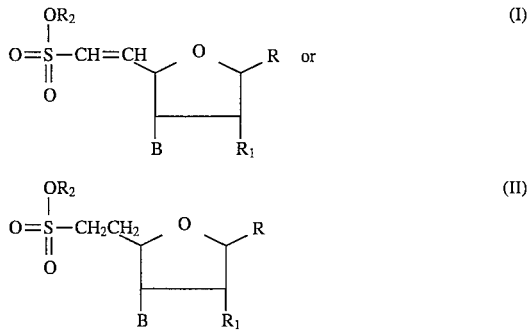

wherein (a) R is purine, pyrimidine, deazapurine or azapurine, or aza or deazapyrimidine optionally substituted by at least one $C_{1-5}$ alkyl, halogen, amino, oxo, hydroxy, or thio group, (b) $R_1$ is hydrogen, hydroxy, $C_{1-5}$ alkoxy, amino optionally substituted by at least one $C_{1-5}$ alkyl, azido, or halogen, (c) $R_2$ is hydrogen, $C_{1-6}$ alkyl or benzyl, (d) B is hydroxy, $NHR_3$ wherein $R_3$ is hydrogen, $C_{1-5}$ alkyl optionally substituted by amino or hydroxy, piperidinyl, piperazinyl, morpholinyl, phenyl, benzyl, allyl, acetyl, or benzoyl or a pharmaceutically acceptable salt thereof.

Figure 1:
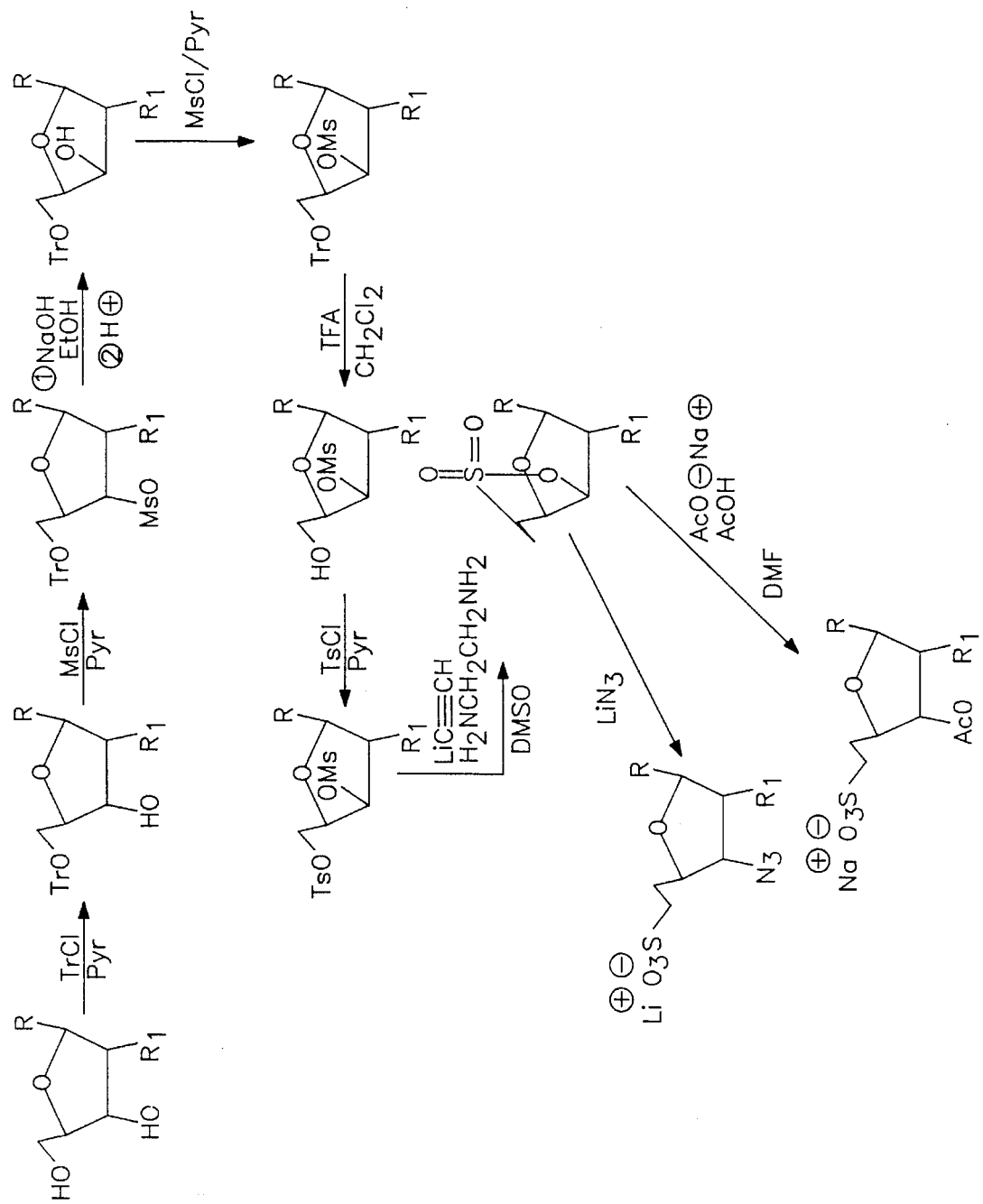
FIG. 1 depicts a synthetic method of preparing the nucleoside monomers of the present invention which incorporates the formation of a sultone ring.

The nucleoside of the present invention can be prepared by homologation of a nucleoside or nucleoside analog. FIG. 1 illustrates homologation of a compound in accordance with the present invention. Generally, the 3' and 5' hydroxyls are protected by a protective group before homologation. A protective group refers to a chemical modification of a reactive functional group. Appropriate protective groups differ depending on the type of group that is to be protected. However, the type of protective group to be employed can be readily determined by one of ordinary skill in the art. (See Greene, *Protective Groups in Organic Synthesis*, Wiley-Interscience, New York (1981), concerning uses of and methods for functional group protection, deprotection, and unmasking.)

It is important that the protective group is capable of being easily introduced, that the group is stable, and that the function of the protected group be restored after chemical transformation. The purpose of the protective group is to "hide" the reactive function of one portion of a molecule while manipulating other, nonrelated portions of the same molecule.

After appropriate protection of the 3' and 5' hydroxyls, homologation can be achieved by intramolecular displacement of the group at the 5'-position, followed by ring opening of the resultant sultone (as in FIG. 1). Homologation can also be accomplished by deblocking at the 5' position followed by oxidation and coupling with a sulfonyl-stabilized Wittig reagent (as in FIG. 2).

In general, deblocking refers to removing the substituent group that was used to "hide" or protect the reactive function of at least one portion of the molecule. Deblocking procedures which are known in the art may be used. (See Greene, supra.)

The sultone ring which results from the intramolecular displacement of the group at the 5'-position may be opened by simple hydrolysis to yield the free 3'-hydroxylic derivative. The sultone ring also may be opened by intermolecular nucleophilic displacement.

Any common nucleophile can be employed for the ring opening. Non-limiting examples are azide, acetate (as shown in FIG. 1), halide, carboxylic acid salts, and cyanide.

Figure 2:
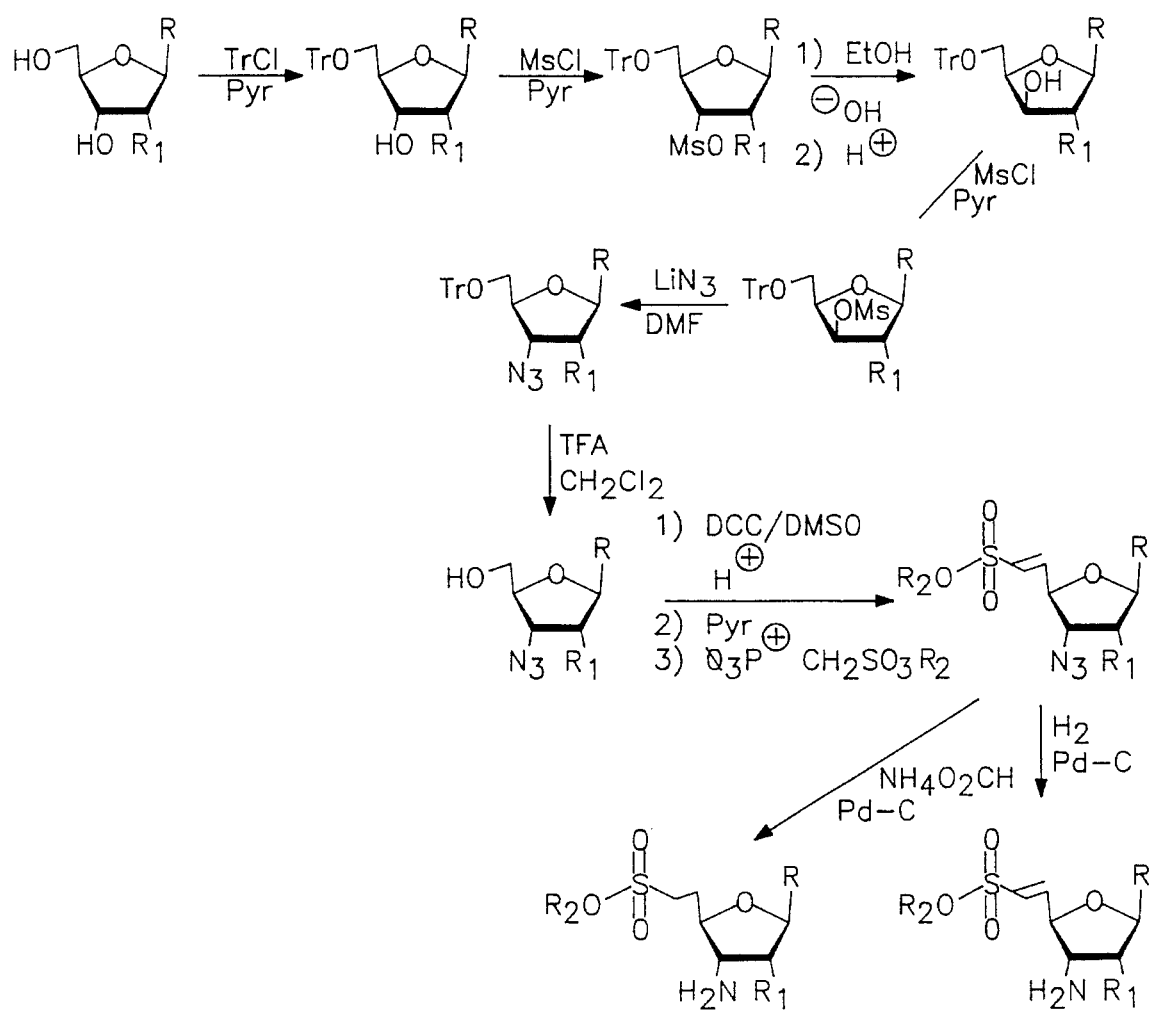
FIG. 2 shows a synthetic method of preparing the nucleoside monomers of the present invention by using a Wittig reagent.

When the Wittig reagent is used, the functional ability of the group at the 3'-position must be incorporated independently of the homologation procedure using standard organic synthesis techniques. This means that the sulfonate oxygen or the sulfonamide nitrogen is incorporated into the nucleoside sugar ring, either in blocked or unblocked form, before the one-carbon extension and the incorporation of sulfur at the 5'-position. As an example, FIG. 2 shows incorporation of a nitrogen function as an $N_3$ substituent, and subsequent modification of the substituent at the 5'-position to introduce the sulfonyl moiety.

The preferred polynucleotide analogs of the present invention have repeating units of the formula

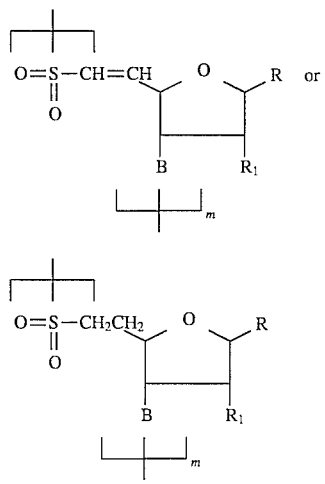

wherein (a) R is purine, pyrimidine, deaza or aza purine or aza, or deaza pyrimidine optionally substituted by at least one $C_{1-5}$ alkyl, halogen, amino, oxo, hydroxy, or thio group, (b) $R_1$ is hydrogen, hydroxy, $C_{1-5}$ alkoxy, amino optionally substituted by at least one $C_{1-5}$ alkyl, azido, or halogen, (c) B is oxygen, $NHR_3$ wherein $R_3$ is hydrogen, $C_{1-5}$ alkyl optionally substituted by amino or hydroxy, piperidinyl, piperazinyl, morpholinyl, phenyl, benzyl, allyl, acetyl, or benzoyl, (d) m is from 2 to 200. Preferably, m is in the range of 6 to 50.

In the preferred nucleoside and the polynucleotide analog of the present invention, the group R is pyrimidine, thymine, uracil, cytosine, N-alkyl- and N,N-dialkylcytosine (wherein alkyl is $C_1$-$C_5$ and may or may not be identical), 2,4-diaminopyrimidine and N-alkylated and N,N'-alkylated derivatives (wherein alkyl is $C_1$-$C_5$ and may or may not be identical), 5-alkyluracil (wherein alkyl is $C_2$-$C_5$), 5-alkylcytosine (wherein alkyl is $C_1$-$C_5$), 4-aminopyrimidine, N-alkyl- and N,N-dialkylaminopyrimidine (wherein alkyl is $C_1$-$C_5$ and may or may not be identical), 5-halopyrimidine (wherein halo is fluoro, chloro, bromo), 5-halomethylpyrimidine (wherein halo is fluoro, chloro, bromo), 4-thiouracil, 2-amino-4-thiopyrimidine, 2-thiocytosine, 2,4-dithiouracil, 4-thio, 2-thio, and 2,4-dithiothymine, 5-hydroxymethylcytosine, 5-hydroxythymine, and the 1-deaza (e.g., the corresponding C-nucleosides), 3-deaza, 2-aza, 5-aza, and 6-aza derivatives thereof; purine 2-aminopurine, adenine, guanine, isoguanine, xanthine, hypoxanthine, 2,6-diaminopurine, 6-thioguanine, 6-thiohypoxanthine, 2-thio, 6-thio, and 2,6-dithiozanthine, 2-thioisoguanine, 8-amino substituted derivatives thereof, as well as the N-alkyl- (wherein alkyl is $C_1$-$C_5$) and N,N-dialkyl- (wherein alkyl is $C_1$-$C_5$ and may or may not be identical) substituted derivatives of adenine, guanine, isoguanine, 2-aminopurine, 2,6-diaminopurine, the 8-amino substituted derivatives thereof, and the corresponding 1-deaza, 3-deaza, 7-deaza, 9-deaza, 2-aza, and 8-aza derivatives thereof. As exemplary halogen for the group $R_1$, F, Cl, Br, or I are included.

As the monosubstituted amino nitrogen, the group RNH— can be incorporated, where R is alkyl ($C_1$-$C_5$), hydroxy- and amino-substituted alkyl (e.g., 2-hydroxyethyl, 2-dimethylaminoethyl).

Figure 3:
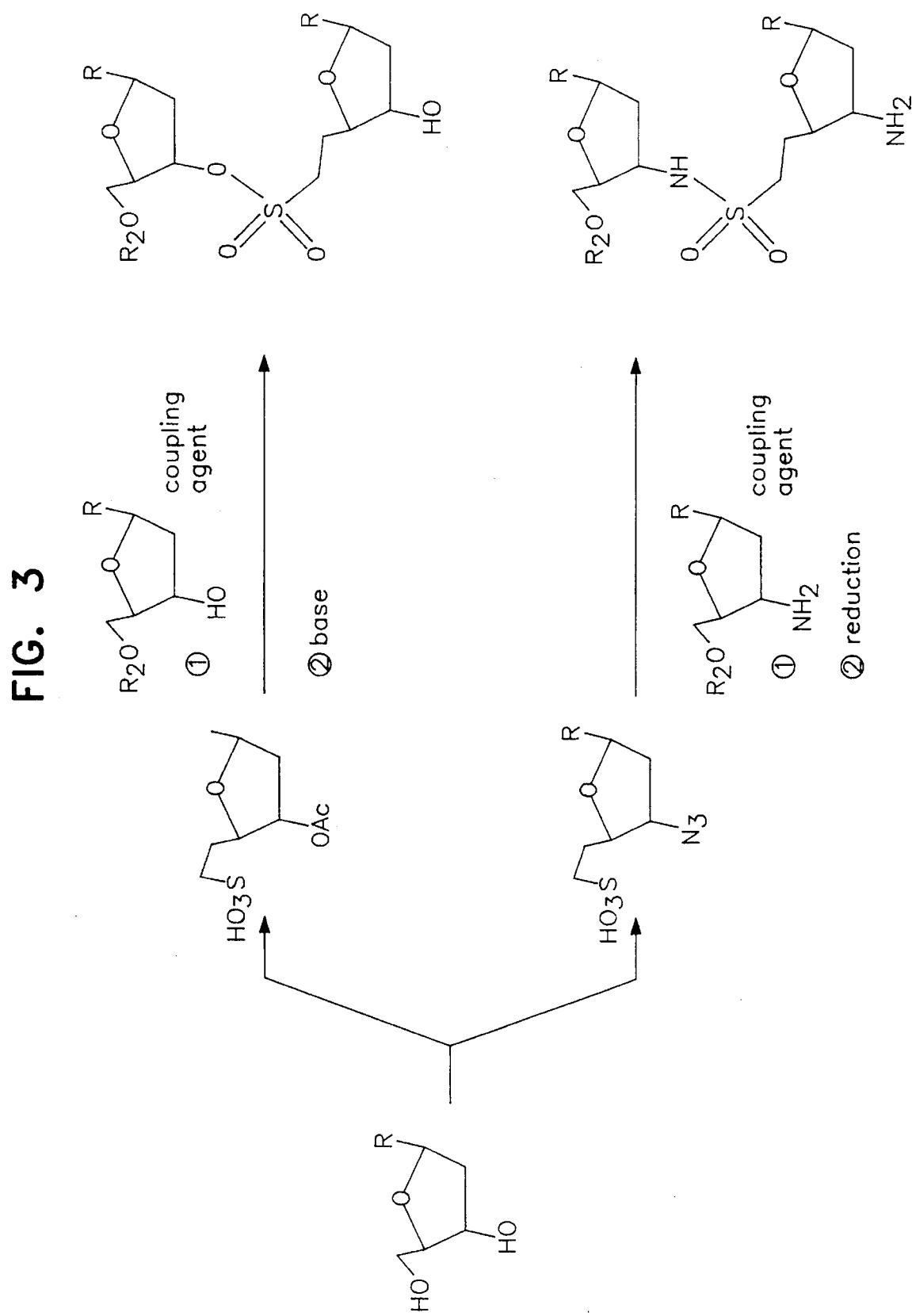
FIG. 3 depicts a synthetic method of preparing the polynucleotide analogs of the present invention.

The polynucleotide analogs of the present invention are prepared by coupling the nucleoside monomers. Initially, the nucleoside monomers are coupled to form dimers. The coupling methodology is achieved with the addition of a coupling agent (as shown in FIG. 3). The dimers which are formed can be used as a building block in the preparation of other polynucleotide analogs of the present invention. The dimers can be extended by repetition of the coupling methodology or by deblocking the group at the 3'-terminus. The deblocking technology allows for mixing of linkage types upon extension.

FIG. 3 outlines the preparation of sulfonamide and sulfonate nucleoside dimers. Coupled sulfonamide dimers such as that shown in FIG. 3 are prepared by dissolving a coupling agent and a sulfonic acid nucleoside in a suitable solvent and adding a 3'-aminonucleoside component. Preferably, the 3'-aminonucleoside is blocked at the 5'-position.

Coupled sulfonate dimers which are shown in FIG. 3 are prepared by dissolving a coupling agent and a sulfonic acid nucleoside in a suitable solvent and adding a 3'-hydroxynucleoside component. Preferably, the 3'-hydroxynucleoside is blocked at the 5'-position. To achieve mixing of linkage types, the 3'-aminonucleoside and the 3'-hydroxynucleoside can be added in alternating or repeating sequences.

As sulfonic acid nucleosides, the monomers of this invention are to be used. Preferred sulfonic acid nucleosides are those which incorporate thymine, cytosine, adenine, and guanine as the base substituent.

Suitable solvents are aprotic solvents, and include pyridine, dichloromethane, chloroform, tetrahydrofuran, diethyl ether, benzene, dioxane, acetonitrile, dimethylformamide, and dimethylsulfoxide.

Any reagent which can be used for condensation of the appropriate 3'-blocked and 5'-blocked components via dehydration (e.g., removal of the elements of water to form the bond) can be used as coupling agents. Preferably, triisopropylbenzenesulfonyl 3-nitrotriazole, triisopropylbenzenesulfonyl chloride, triphenylphosphine ditriflate, triphenyldichlolorphosphorane, carbodiimides (e.g., dicyclohexylcarbodiimide, diisopropylcardbodiimide, and di-t-butylcarbodiimide), 2-6-substituted benzenesulfonyl chlorides and 2,6-substituted benzenesulfonyl azoles (e.g., 2,4,6-triisopropylbenzensulfonyl imidazole, triisopropylbenzensulfonyl tetrazole, triisopropylbenzensulfonyl triazole, triisopropylbenzensulfonyl 3-nitrotriazole, triisopropylbenzensulfonyl chloride, mesitylenesulfonyl chloride, mesitylenesulfonyl triazole, mesitylenesulfonyl 3-nitrotriazole, 2,6-di-t-butylbenzenesulfonyl chloride), trialkylphosphoranes (e.g., triphenyldibromophosphorane, triphenyldichlorophosphorane, and triphenylphosphine ditriflate), carbonyl diazoles (e.g., carbonyl diimidazole, carbonyl ditriazole, and carbonyl di-3-nitrotriazole) and phosphoric amides (e.g., bis(2-oxo-3-oxazolidinyl)phosphinic chloride and benzotriazol-1-yloxytris(dimethylamino)phosphonium hexafluorophosphate [BOP reagent]) can be used. The coupling agent triphenylphosphine ditriflate is prepared in situ from triphenylphosphine oxide and trifluoromethanesulfonic anhydride.

A 5'-blocked 3'-aminonucleoside can be:

(1) A nucleoside or a nucleoside analog as defined above, wherein B is $N_3$, $NH_2$ or $NHR_3$. In the present case, since homologation at the 5' position has not occurred, the monomer would act as the 5'-terminal residue, and the 5'-hydroxyl would be protected by trityl, monomethoxytrityl, dimethoxytrityl, or trialkylsilyl (e.g., t-butyldimethylsilyl, t-butyldiphenylsilyl, and triisopropylsilyl);

(2) A 5'-homologated nucleoside sulfonic acid or sulfonate salt, as defined by the formulas above wherein B is $N_3$, $NH_2$ or $NHR_3$. In the present case, the 5'-protecting group would be an alkyl ester of the nucleoside sulfonic acid (e.g. wherein alkyl is methyl, ethyl, n-propyl, iso-propyl, n-butyl, sec-butyl, t-butyl, pentyl, benzyl, or nitrophenyl); or (3) An oligomer as defined by the polynucleotide analog above, wherein the 5'-terminal residue is blocked as described in (1) or (2), and the 3'-terminus is a free amino or alkyl amino moiety as described by the group B, wherein B is $N_3$, $NH_2$ or $NHR_3$.

A 5'-blocked 3'-hydroxynucleoside can be:

(1) A nucleoside or a nucleoside analog as defined above, wherein B is hydroxy. In the present case, since homologation at the 5' position has not occurred, the monomer would act as the 5'-terminal residue, and the 5'-hydroxyl would be protected by trityl, monomothoxytrityl, dimethoxytrityl, or trialkylsilyl (e.g., t-butyldimethylsilyl, t-butyldiphenylsilyl, and triisopropylsilyl);

(2) A 5'-homologated nucleoside sulfonic acid or sulfonate salt, as defined by the formulas above wherein B is hydroxy. In the present case, the 5'-protecting group would be an alkyl ester of the nucleoside sulfonic acid (e.g. wherein alkyl is methyl, ethyl, n-propyl, iso-propyl, n-butyl, sec-butyl, t-butyl, pentyl, benzyl, or nitrophenyl); or (3) An oligomer as defined by the polynucleotide analog above, wherein the 5'-terminal residue is blocked as described in (1) or (2), and the 3'-terminus is a free amino or alkyl amino moiety as described by the group B, wherein B is hydroxy.

Figure 4:
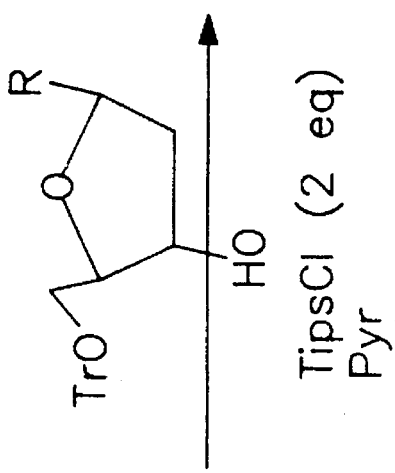
FIG. 4 shows a deblocking process which allows for mixing of sulfonate and sulfonamide linkages.
Figure 4:
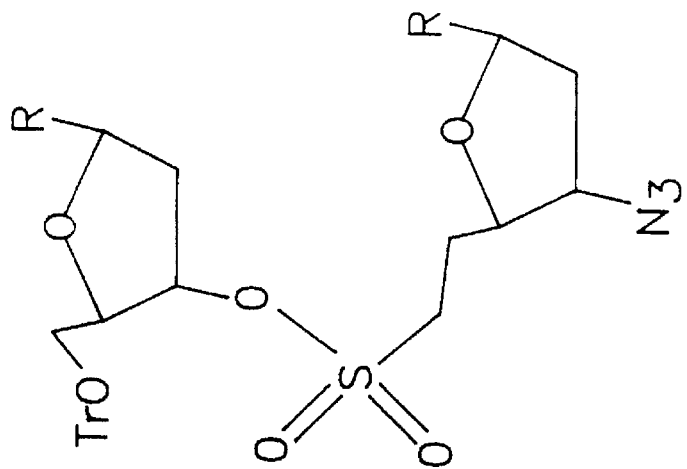
Figure 4:
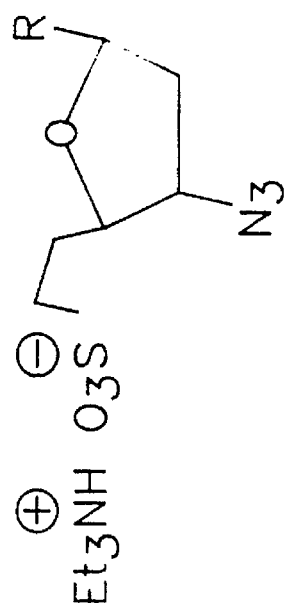

Mixing of linkage types can be accomplished by deblocking the 3'-aminonucleoside component. FIG. 4 illustrates the methodology by which deblocking and subsequent coupling is accomplished. The figure shows that a 3'-aminonucleoside is unmasked and coupled to a 3'-hydroxynucleoside using a coupling agent. Deblocking of the 3'-aminonucleoside is accomplished by reduction of the terminal azido function by heterogeneous hydrogenation using a catalyst (e.g., palladium of platinum on carbon), or by homogeneous methods (e.g., trialkylphosphine reduction). As coupling agents, the compounds used in the preparation of the sulfonamide and sulfonate nucleoside dimers can be used.

Polynucleotide analogs are prepared using the sulfonamide and sulfonate dimers as building blocks. The dimers are extended by repeating the steps of the coupling methodology or by the deblocking methodology. By alternating the coupling and deblocking methodologies, a polynucleotide analog having mixed sulfonate and sulfonamide linkages can be obtained.

Preferred embodiments of the present invention can be prepared according the following, non-limiting examples.

EXAMPLE 1

The sultone product of FIG. 1 is prepared as follows:

A solution of 5.0 g (20.6 mmoles) of thymidine in 100 ml of dry pyridine containing 7.0 g (25.1 mmoles) of triphenylmethyl chloride is heated at 100° C. with stirring for 0.5 hours. The cooled reaction mixture is poured into 1.5 l of ice water with vigorous stirring. The reaction product is collected, washed with water, and dried.

Methanesulfonyl chloride (2.5 ml) is added to a solution of 5'-tritylthymidine (5 g) in pyridine (50 ml), and kept overnight at 0° C. Ice water (1 ml) is added and after 1 hour at 0° C. the mixture is poured into ice water (500 ml). The precipitate is filtered off, washed with water, and dried.

To a solution of 4.0 g (7.15 mmoles) of 3'-O-mesyl-5'-O-tritylthymidine in 100 ml of ethanol containing 28.5 ml of 1N sodium hydroxide is added 100 ml of water and the solution is refluxed for 4 hours. The reaction mixture is concentrated to ca. 100 ml in vacuo, chilled by the addition of ice, and carefully acidified (pH 2) with dilute hydrochloric acid. The amphorous colorless material is collected, washed with water and crystallized from ethanol.

To a cold solution of 9.0 g (18.6 mmoles) of 1-(2-deoxy-5-O-trityl-β-D-lyxosyl)thymine in 50 ml dry pyridine is added 4.2 ml (57.2 mmoles) of methanesulfonyl chloride and the reaction mixture is held at 0° C. for 16 hours. The solution is allowed to reach room temperature and is held there for 3 hours. The mixture is re-cooled to 0° C., treated with ca. 2 ml ice water, refrigerated for 1 hour, and poured slowly, with vigorous stirring, into 1.5 l of ice water. After 1 hour of stirring the reaction product is collected, dried, and crystallized from ethanol.

Trifluoroacetic acid (12.0 ml) and dichloromethane (40 ml) are stirred together, and 1-(2-deoxy-3-O-mesyl-5-O-trityl-β-D-lyxosyl)thymine (6.0 g) is added. After 5 minutes the reaction is quenched by pouring into hexane (300 ml). The yellow supernate is separated and the residual oil triturated with dry hexane to give a semisolid which is recrystallized from ethanol.

1-(2-deoxy-3-O-mesyl-β-D-lyxofuranosyl)thymine (0.5 g) is dissolved in dry pyridine (4 ml) containing p-toluenesulfonyl chloride (0.32 g) and 4-(N,N-dimethylamino)pyridine (3 mg), and the mixture stirred at room temperature for 16 hours. The reaction mixture is then poured into ice water (40 ml) with vigorous stirring. The gum crystallizes with scratching.

1-(2-deoxy-3-O-mesyl-5-O-tosyl-β-D-lyxosyl)thymine (0.5 g) and lithium acetylide ethylene diamine complex (0.224 g) are mixed together and dry dimethylsulfoxide (7 ml) added. The mixture is stirred at ambient temperature for 2 hours. The mixture is poured into water (50 ml) containing 0.5 ml of 80% aqueous acetic acid. The resulting solution is extracted with ethyl acetate (3×150 ml) and the pooled organic layers washed with water (100 ml) and dried over $MgSO_4$. Evaporation of the solvent and trituration of the residue with methanol/ether affords the sultone product as a colorless crystalline powder.

EXAMPLE 2

Preparation of the 3'-azidonucleoside sulfonic acid (lithium salt) is as follows:

A solution of 1-(2,5,6-trideoxy-β-D-xylohexofuranosyl-3,6-sultone)thymine (30 mg) in N,N-dimethylformaminde (0.5 ml) containing lithium azide (10 mg) is stirred at 80°–100° C. under nitrogen for 12 hours. After cooling to room temperature, solvent is removed in vacuo. The residue is taken up in 0.1M triethylammonium acetate buffer and purified by column chromatography.

EXAMPLE 3

Preparation of the 3'-acetylnucleoside sulfonic acid (sodium salt) is as follows:

A solution of 1-(2,5,6-trideoxy-β-D-xylohexofuranosyl-3,6-sultone)thymine (100 mg) and sodium acetate (100 mg) dissolved in N,N-dimethylformamide (5 ml) is heated at 100° C. for 48 hours. Solvent is removed in vacuo, leaving a white solid. The solid is taken up in 0.1M triethylammonium acetate buffer and purified by column chromatography.

EXAMPLE 4

Preparation of a sulfonate ester dimer is as follows:

The trialkylammonium salt of 1-(2,5,6-trideoxy-3-O-acetyl-β-D-ribohexofuranosyl-6-sulfonic acid)thymine is repeatedly evaporated from dry pyridine, then dissolved in dry pyridine (10 ml) under argon atmosphere. To this solution is added 934 mg (2.0 equivalents) of triisopropylbenzensulfonyl chloride, and the mixture stirred for 1 hour. Thereupon 1.0 equivalent (731 mg) of 5'-tritylthymidine is added, and stirred for 16 hours. The mixture is poured into 500 ml ice water, and the resulting tan, opaque solid extracted into dichloromothane (4×100 ml). The solution is washed with water, dried over anhydrous sodium sulfate, and evaporated to dryness. The product is purified by silica gel chromatography.

EXAMPLE 5

Preparation of a sulfonamide dimer is as follows:

The triethylammonium salt of 1-(2,3,5,6-tetradeoxy-3-azido-β-D-ribohexofuranosyl-6-sulfonic acid)thymine (1.0 g) is repeatedly dissolved (5 times) in acetonitrile (10 ml) and diisopropylethylamine (1 ml) and evaporated carefully under high vacuum. The resulting oil is dissolved in $CH_2Cl_2$ (10 ml) and evaporated on a rotary evaporator and dried to constant weight under high vacuum yielding a dry tractable foam. A portion of the solid foam (145 mg) is dissolved in dry $CH_2Cl_2$ (2 ml) and added at 0° C. to a solution of triphenylphosphine ditriflate (1.1 equivalent in 5 ml $CH_2Cl_2$) prepared according to the procedure of Hendrichson and Hussoin (J. Org. Chem. 1989, 54, 1144). The resulting solution is kept at 0° C. for one hour and added dropwise to a stirred solution of 3'-amino-5'-tritylthymidine (1.1 eq.) and diisopropyl ethylamine (1 eq.) in $CH_2Cl_2$ (2 ml) at 0° C. The reaction is allowed to warm to room temperature and was stirred overnight. The product is isolated by preparative layer chromatography using chloroform:methanol 95:5) as the eluant.

EXAMPLE 6

Conversion of the 3'-azido masking group to a 3'-amino function to form mixed linkages is as follows:

The 3'-azido terminated dimer of Example 2 (45 mg) is added to a solution of 97 mg of triphenylphosphine and 1.3 ml of freshly distilled methanol containing 74 ml of triethylamine. This mixture is left for 20 hours and then tributylamine was added (40 ml); and the reaction is left another eight hours, concentrated, and the product is isolated by preparative layer chromatography using chloroform:methanol (3:1) as the eluant.

EXAMPLE 7

The methylated oligophosphate sequence 5'-d(TCC-CAG-GCT-CAG-ATC-TGG-TC)- 3' is prepared as in Example 6. Anti-HIV activity is ascertained by the following procedure:

The synthesized analog is diluted and added to wells of a 96-well round bottom microtiter plate in a volume of 100 μl. CD4 cells expressing T-lymphoblast cell line CEM are added to each well at a concentration of $5\times10^3$ cells per well in a volume of 50 μl. 50 μl of HIV-1 are added to each well. Virus stocks are prepared and frozen at −120° C. until use. The multiplicity of infection for the assay is 0.05.

The plates are incubated for 6 days at 37° C. in a $CO_2$ incubator. On day 6, 50 μl of the supernate is harvested from each well and cells and cell debris removed by centrifugation. This sample is utilized for confirmation testing. Following the removal of the sample, 50 μl of the tetrazolium reagent 2,3-bis-[2-methoxy-4-nitro-5-sulfophenyl]-5-[(phenylamino)carbonyl]-2H-tetrazolium hydroxide (XTT) is added to each well. Absorption is measured at 490 nm. It is found that a significant number of wells have an optical density greater than 1.0 which indicates viable, metabolically active cells.

What is claimed is:

1. A compound of the formula

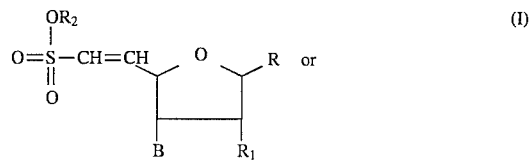

(I)

or

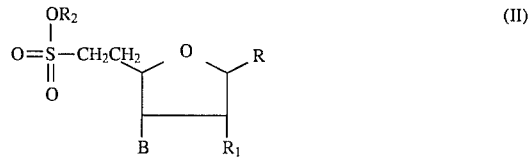

(II)

wherein:

(a) R is purine, pyrimidine, deaza or aza purine, or aza or deaza pyrimidine optionally substituted by at least one $C_{1-5}$ alkyl, halogen, amino, oxo, hydroxy, or thio group, (b) $R_1$ is hydrogen, hydroxy, $C_{1-5}$ alkoxy, amino optionally substituted by at least one $C_{1-5}$ alkyl, azido, or halogen, (c) $R_2$ is hydrogen, $C_{1-6}$ alkyl or benzyl, (d) B is hydroxy or $NHR_3$ wherein $R_3$ is hydrogen, $C_{1-5}$ alkyl optionally substituted by amino or hydroxy, piperidinyl, piperazinyl, morpholinyl, phenyl, benzyl, allyl, acetyl, or benzoyl, or a pharmaceutically acceptable salt thereof, provided that in the compound (II) both B and $R_1$ are not hydroxy.

2. The compound of claim 1, wherein R is adenine, guanine, cytosine, thymine, or uracil.

3. The compound of claim 1, wherein $R_1$ is hydrogen or hydroxy.

4. The compound of claim 1, wherein B is hydroxy.

5. The compound of claim 1 wherein B is $NHR_3$ and $R_3$ is hydrogen, $C_{1-5}$ alkyl optionally substituted by amino or hydroxy, piperidinyl, piperazinyl, morpholinyl, phenyl, benzyl, allyl, acetyl, or benzoyl.

6. A polynucleotide analog having repeating units of the formula

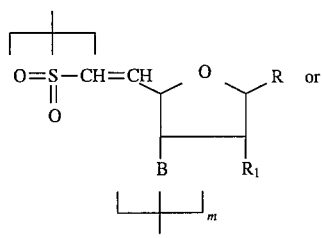
(III)

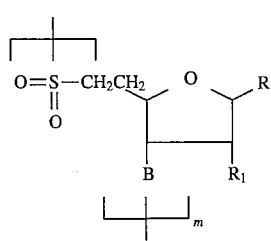
(IV)

wherein:
(a) R is independently in each unit purine, pyrimidine, deaza or aza purine, or aza or deaza pyrimidine, where R is optionally substituted by at least one $C_{1-5}$ alkyl, halogen, amino, oxo, hydroxy, or thio group, (b) $R_1$ is independently in each unit hydrogen, hydroxy, $C_{1-5}$ alkoxy, amino optionally substituted by at least one $C_{1-5}$ alkyl, azido, or halogen, (c) B is independently in each unit oxygen or $NR_3$ wherein $R_3$ is hydrogen, $C_{1-5}$ alkyl optionally substituted by amino or hydroxy, piperidinyl, piperazinyl, morpholinyl, phenyl, benzyl, allyl, acetyl, or benzoyl, and (d) m is from 2 to 200;

a 5'-end unit of the formula

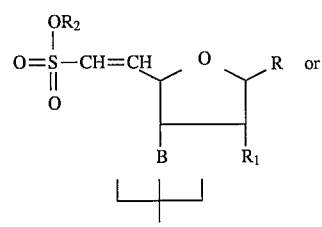
(III)$_a$

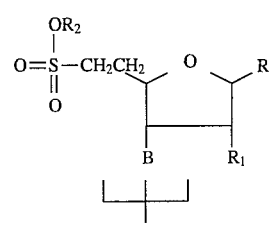
(IV)$_a$ wherein R, $R_1$, and B are as defined above and $R_2$ is hydrogen, $C_{1-6}$ alkyl or benzyl;

a 3'-end unit of the formula

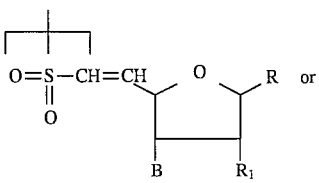
(III)$_b$

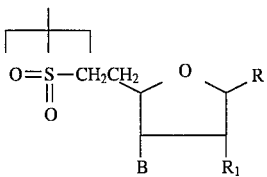
(IV)$_b$ wherein R and $R_1$ are as defined above and B is hydroxy or $NHR_3$ wherein $R_3$ is hydrogen, $C_{1-5}$ alkyl optionally substituted by amino or hydroxy, piperidinyl, piperazinyl, morpholinyl, phenyl, benzyl, allyl, acetyl, or benzoyl; or a pharmaceutically acceptable salt thereof, provided that in the formula (IV)$_b$, both B and $R_1$ are not hydroxy.

7. A method of making a compound of the formula

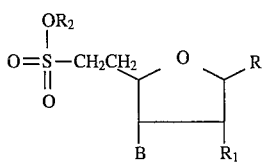
(II)

wherein R is purine, pyrimidine, deazapurine or azapurine or aza, or deazapyrimidine optionally substituted by at least one $C_{1-5}$ alkyl, halogen, amino, oxo, hydroxy, or thio group; $R_1$ is hydrogen, hydroxy, $C_{1-5}$ alkoxy, amino optionally substituted by at least one $C_{1-5}$ alkyl azido, or halogen; $R_2$ is hydrogen, $C_{1-6}$ alkyl or benzyl; B is hydroxy or $NHR_3$ wherein $R_3$ is hydrogen, $C_{1-5}$ alkyl optionally substituted by amino or hydroxy, piperidinyl, piperazinyl, morpholinyl, phenyl, benzyl, allyl, acetyl, or benzoyl; or a pharmaceutically acceptable salt thereof, comprising:

a) intramolecular displacement at the 5'-O position of a nucleoside wherein lithium acetylide ethylene diamine complex and dimethylsulfoxide are reacted with a 5'-O protected nucleoside compound to form a sultone ring at the 5' and 3' positions, and (b) opening the sultone ring to obtain the compound of formula (II).

8. The method of claim 7, wherein the sultone ring is opened by hydrolysis or intermolecular nucleophilic displacement.

9. A method of making a compound of the formula

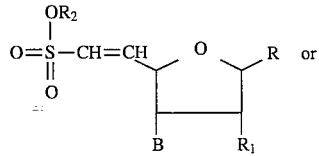
(I)

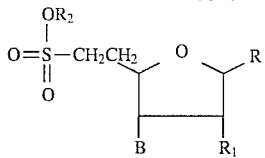

(II)

wherein R is purine, pyrimidine, deaza or aza purine or aza, or deaza pyrimidine optionally substituted by at least one $C_{1-5}$ alkyl, halogen, amino, oxo, hydroxy, or thio group; $R_1$ is hydrogen, hydroxy, $C_{1-5}$ alkoxy, amino optionally substituted by at least one $C_{1-5}$ alkyl, azido, or halogen; $R_2$ is hydrogen, $C_{1-6}$ alkyl or benzyl; B is hydroxy or $NHR_3$ wherein $R_3$ is hydrogen, $C_{1-5}$ alkyl optionally substituted by amino or hydroxy, piperidinyl piperazinyl, morpholinyl, phenyl, benzyl, allyl, acetyl, or benzoyl; and, n is 1 or 2, or a pharmaceutically acceptable salt thereof, comprising:

reacting a compound of the formula

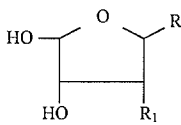

wherein R and $R_1$ are defined as in formulae (I) and (II), with a sulfonyl-stabilized Wittig reagent.

10. A method of making a polynucleotide analog comprising, (a) dissolving in a suitable solvent a coupling agent and a compound of the formula,

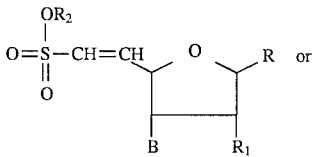

(I)

or

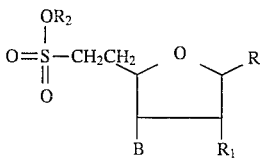

(II)

wherein R is purine, pyrimidine, deazapurine or azapurine or aza, or deazapyrimidine optionally substituted by at least one $C_{1-5}$ alkyl, halogen, amino, oxo, hydroxy, or thio group; $R_1$ is hydrogen, hydroxy, $C_{1-5}$ alkoxy, amino optionally substituted by at least one $C_{1-5}$ alkyl, azido, or halogen; B is hydroxy or $NHR_3$ wherein $R_3$ is hydrogen, $C_{1-5}$ alkyl optionally substituted by amino or hydroxy, piperidinyl, piperazinyl, morpholinyl, phenyl, benzyl, allyl, acetyl, or benzoyl; or a pharmaceutically acceptable salt thereof, and (b) adding a 3'-aminonucleoside or a 3'-hydroxynucleoside.

11. The method of claim 10, wherein the 3'-aminonucleoside and the 3'-hydroxynucleoside are added in alternating or repeating sequences.

12. The method of claim 10, wherein the solvent is selected from the group consisting of pyridine, dichloromethane, chloroform, tetrahydrofuran, diethyl ether, benzene, dioxane, acetonitrile, dimethylformamide, and dimethylsulfoxide.

13. The method of claim 10, wherein the 3'-aminonucleoside and the 3' hydroxynucleoside are blocked at the 5'-position.

14. A method of making a polynucleotide analog comprising dissolving in a suitable solvent a coupling agent and a nucleotide analog wherein the 5' carbon is covalently bonded to a group of the formula —$CH_2SO_2OH$ or =$CHSO_2OH$ and adding a 3'-aminonucleoside or 3'-hydroxynucleoside.

15. A method of making a polynucleotide analog wherein the 3' and 5' ends of adjacent nucleosides therein are linked through moieties as in the formula 3'-B—$SO_2$—$CH_2$-5' or 3'-B—$SO_2$—CH=5' wherein B is independently in each moiety oxygen or $NR_3$ with $R_3$ being hydrogen, $C_{1-5}$ alkyl optionally substituted by amino or hydroxy, piperidinyl, piperazinyl, morpholinyl, phenyl, benzyl, allyl, acetyl, or benzoyl, comprising:

(a) dissolving, in a suitable solvent, a coupling agent and a nucleotide analog wherein the 5' carbon is covalently bonded to a group of the formula —$CH_2SO_2OH$ or =$CHSO_2OH$, and (b) adding a 3'-aminonucleoside or a 3'-hydroxynucleoside.

16. A polynucleotide analog wherein the 3' 5' ends of adjacent nucleosides therein are linked through moieties as in the formula 3'-B—$SO_2$—$CH_2$-5' or 3'-B—$SO_2$—CH=5' wherein B is independently in each moiety oxygen or $NR_3$ with $R_3$ being hydrogen, $C_{1-5}$ alkyl optionally substituted by amino or hydroxy, piperidinyl, piperazinyl, morpholinyl, phenyl, benzyl, allyl, acetyl, or benzoyl.

* * * * *